United States Patent [19]

Galet et al.

[11] Patent Number: 5,246,951

[45] Date of Patent: Sep. 21, 1993

[54] NEW BENZOSELENAZOLINONE COMPOUNDS

[75] Inventors: Vincent Galet, Coudekerque Branche; Marie-Pierre Vaccher, Wattignies; Daniel Lesieur, Gondecourt; Pierre Renard, Versailles; Daniel H. Caignard, Paris; Jean-Francois Renaud de la Faverie, Le Chesnay; Gérard Adam, le Mesnil le Roi, all of France

[73] Assignee: Adir et Compagnie, Courbevoie, France

[21] Appl. No.: 796,457

[22] Filed: Nov. 22, 1991

[30] Foreign Application Priority Data

Nov. 23, 1990 [FR] France .................. 90 14591

[51] Int. Cl.⁵ .................. C07D 293/12; C07C 391/02; A61K 31/17; A61K 31/41
[52] U.S. Cl. .................. 514/359; 514/598; 514/640; 548/121; 562/899
[58] Field of Search ............... 548/121, 100; 562/899; 514/359, 598, 640

[56] References Cited

U.S. PATENT DOCUMENTS 3,417,082 12/1968 Taylor .................. 548/100

OTHER PUBLICATIONS

Clark, J. Chem. Soc. 2805 (1927).
Hasan, J. Chem. Soc. 1762 (1935).

*Primary Examiner*—Robert Gerstl
*Attorney, Agent, or Firm*—Gordon W. Hueschen

[57] ABSTRACT

Compounds of general formula (I):

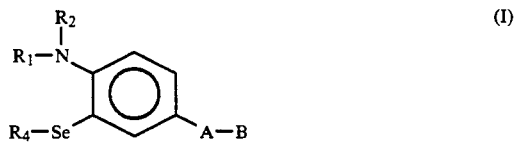

where $R_1$, $R_2$, $R_4$, A and B are defined in the description. Medicinal products.

20 Claims, No Drawings

NEW BENZOSELENAZOLINONE COMPOUNDS

The present invention relates to new benzoselenazolinone compounds, to a process for preparing these and to pharmaceutical compositions containing them.

European Patent Application 0,044,971 describes the antirheumatic activity of 2-phenyl-1,2-benzisoselenazol-3(2H)-one. The present invention has discovered new benzoeselenazol-2(3H)-one, or benzoselenazolinone, compounds whose activity in various tests revealing an antioxidant activity is markedly greater than that of the compound referred to in Patent Application EP 0.044,971. This improved level of activity, linked to the low toxicity of the compounds of the invention, enables smaller doses to be administered, this being especially advantageous in view of the chronic nature of the treatment of the diseases for which the compounds of the invention are likely to be administered. In addition, the compounds of the invention have shown good platelet aggregation-inhibitory and immunostimulatory properties, which make them advantageous in therapeutic indications different from those mentioned in Application EP 0,044,971.

More specifically, the invention relates to compounds of general formula (I):

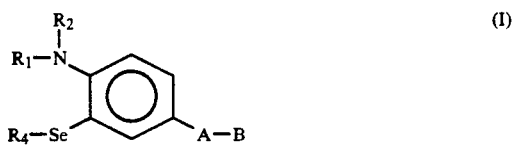

in which:

$R_1$ represents either a hydrogen atom or a group $CO-NR_7R_8$, with $R_7$ and $R_8$, which may be identical or different, representing a hydrogen atom, a lower alkyl or a cycloalkyl group having 3 to 8 carbon atoms or an aryl or substituted aryl or aryl(lower alkyl) or substituted aryl(lower alkyl) group, or, with the nitrogen atom which carries them, forming a heterocyclic system, $R_4$ represents a group:

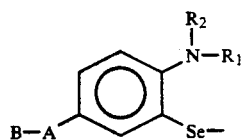

or alternatively:

$R_4$ forms a $-C=O$ group with $R_1$, $R_2$ represents a hydrogen atom or a lower alkyl group optionally substituted with one or more halogen atoms with a hydroxyl group or, when $R_1$ forms a CO group with $R_4$, substituted with a group $NR_5R_6$, in which $R_5$ and $R_6$, which may be identical or different, each represent, independently of one another, a hydrogen atom, a lower alkyl group, an aryl group, a substituted aryl group, an aryl(lower alkyl) group or a substituted aryl (lower alkyl) group, or alternatively $R_5$ and $R_6$, with the nitrogen atom which carries them, form a heterocyclic system, A represents a CO, CHOH or $CH_2$ group, B represents a hydrogen atom, a lower alkyl group, a cycloalkyl group having 3 to 8 carbon atoms, a lower alkenyl group, a lower alkynyl group, an aryl group or a substituted aryl group, a heteroaryl group or a substituted heteroaryl group, an aryl(lower alkyl) group, a heteroaryl(lower alkyl) group or a substituted heteroaryl(lower alkyl) group, a styryl group or a substituted styryl group, or A and B together represent a hydrogen atom, on condition that, when A and B together form a hydrogen atom;

if $R_1$ forms a CO group with $R_4$, then $R_2$ cannot represent either a methyl group or a hydrogen atom, if $R_1$ does not form a CO group with $R_4$, then $R_1$ and $R_2$ cannot simultaneously represent a hydrogen atom, on the understanding that:

the term heterocyclic occurring in the definitions of $R_1$ and $R_2$ represents a mono- or bicyclic system, each ring being five- to six-membered and including in its carbon skeleton one or optionally several identical or different hetero atoms selected from nitrogen, oxygen or sulfur, and optionally substituted with a lower alkyl group, with an aryl group, with an aryl group substituted with an arylalkyl group, with a substituted arylalkyl group; with a heteroaryl group, with a substituted heteroaryl group; with one or more halogen atoms or with a lower alkoxy group, the term substituted qualifying the aryl, aryl(lower alkyl), heteroaryl and styryl groups in the definitions of $R_1$, $R_2$ and B means that these are substituted on the aromatic portion with one or more identical or different groups selected from lower alkyl, lower alkoxy, hydroxyl, trifluoromethyl, amino or carboxyl or with one or more halogen atoms, lower alkyl, lower alkoxy, lower alkenyl and lower alkynyl groups are understood to mean linear or branched groups comprising from 1 to 6 carbon atoms, aryl group is understood to mean a group selected from phenyl or naphthyl, heteroaryl group is understood to mean a mono- or bicyclic aromatic group each ring being five- or six-membered, the two rings collectively including in their carbon skeleton from one to three hetero atoms selected from nitrogen, oxygen or sulfur, their isomers, epimers and diastereoisomers, as well as, when B comprises a carboxyl or phenolic hydroxyl group or when $R_1$ represents a hydrogen atom, their addition salts with a pharmaceutically acceptable base, as well as, when $R_2$ represents an amino group, their addition salts with a pharmaceutically acceptable acid.

Among pharmaceutically acceptable acids which can, where appropriate, be added to the compounds of formula (I) which contain an amino group, hydrochloric, sulfuric, tartaric, maleic, fumaric, oxalic, methanesulfonic and camphoric acids, and the like, may be mentioned without implied limitation.

Among pharmaceutically acceptable bases which can, where appropriate, be added to the compounds of formula (I) containing a carboxylic acid group or a phenolic hydroxyl group in order to obtain a salt, or when $R_1$ represents a hydrogen atom, sodium, potassium, calcium or aluminum hydroxides, alkali metal or alkaline earth metal carbonates or organic bases such as triethylamine, benzylamine, diethylamine, tert-butylamine, dicyclohexylamine, arginine, and the like, may be mentioned without implied limitation.

The subject of the present invention is also the process for preparing the compounds of formula (I), wherein a compound of formula (II):

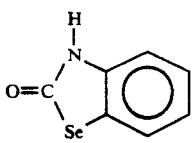
(II)

described in J. Chem. Soc. 1935 (1765) (Hasan and Hunter),
is used as the starting material, which compound can, depending on the nature of $R_2$ in the product of formula (I) which it is desired to obtain, be alkylated on the nitrogen with an alkylating agent to yield a compound of formula (II'):

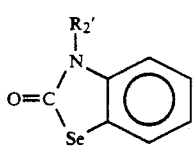
(II')

in which $R_2$, represents a lower alkyl group, which compound of formula (II) or (II') is subjected, depending upon the nature of the substituent B in the compound of formula (I) which it is desired to obtain:
either to the action of an acid of formula (III):

B COOH (III)

in which B has the same definition as in the formula (I), in the presence of polyphosphoric acid,
or to the action of an acid chloride of formula (IV):

Cl COB (IV)

in which B has the same definition as in the formula (I), or alternatively to the action of an acid anhydride of formula (V):

O(COB)$_2$ (V)

in which B has the same definition as in the formula (I), in the presence of dimethylformamide and aluminum chloride, to obtain a compound of formula (I/A):

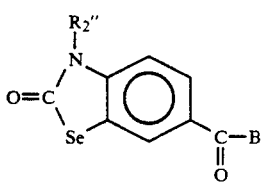
(I/A)

a special case of the compounds of formula (I) in which $R_2''$ represents a hydrogen atom or a lower alkyl group, B has the same meaning as in the formula (I), A represents a CO group and $R_1$ forms a C=O group with $R_4$, which is purified if necessary, which is separated, where appropriate, into its isomers and which is salified, where appropriate, if so desired, with a pharmaceutically acceptable base, which compound (I/A) can, if so desired, be subjected to the action of an alkali metal mixed hydride to yield a compound of formula (I/B):

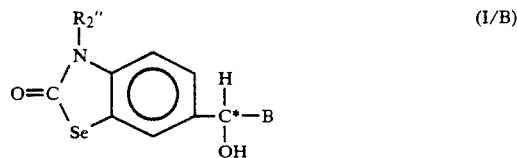
(I/B)

a special case of the compounds of formula (I) in which $R_2''$ has the same meaning as above, B has the same meaning as in the formula (I), A represents a CHOH group and $R_1$ forms a CO group with $R_4$, which is purified if necessary, which is separated, if so desired into its isomers and which is salified, where appropriate with a pharmaceutically acceptable base, which compound of formula (I/A) can also, if so desired, be subjected to the action of a trialkylsilane in an acid medium,
to yield a compound of formula (I/c):

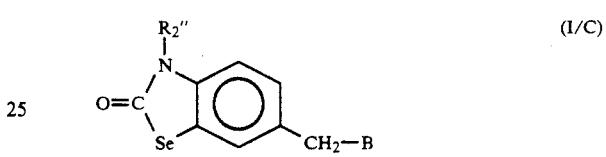
(I/C)

a special case of the compounds of formula (I) in which $R_2''$ and B have the same meaning as above, A represents a $CH_2$ group and $R_1$ forms a CO group with $R_4$, which is purified if necessary, which is separated, where appropriate, into its isomers and which is salified, where appropriate, with a pharmaceutically acceptable base, which compound of formula (I/A), (I/B) or (I/C) can, when $R_2''$ represents a hydrogen atom, be treated:
either with an alkylating agent to obtain a compound of formula (I/D):

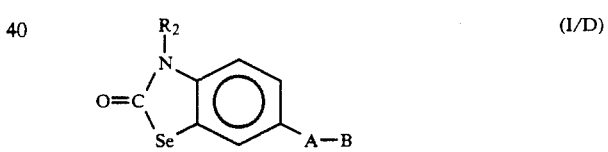
(I/D)

a special case of the compounds of formula (I) in which A and B have the same meaning as in the formula (I) and $R_2$ represents a linear or branched lower alkyl group,
or with an alkaline agent and then with a compound of formula (VI):

$X_1-M-X_2$ (VI)

in which $X_1$ and $X_2$ are different and each represents a halogen atom and M represents a linear or branched lower alkyl group, to yield a compound of formula (I/E):

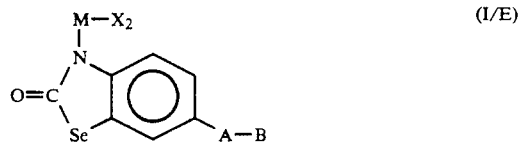
(I/E)

in which A, B, $X_2$ and M have the same definition as above, a special case of the compounds of formula (I)

for which $R_2$ represents a lower haloalkyl group and $R_2$ forms a CO group with $R_4$, which is purified, if necessary, and which is condensed, if so desired, with an amine of formula (VIII):

$$NR_5R_6 \qquad (VIII)$$

in which $R_5$ and $R_6$ have the same definition as in the formula (I), to obtain a product of formula (I/F):

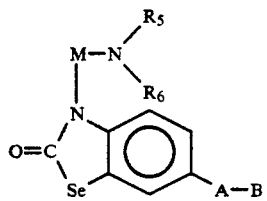

(I/F)

a special case of the compounds of formula (I) in which A and B have the same meaning as in the formula (I) and $R_2$ represents a lower alkyl group substituted with a group $NR_5R_6$, or, after the action of an alkaline agent, with a compound of formula (IX):

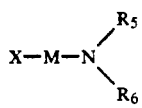

(IX)

in which X represents a halogen atom and M, $R_5$, and $R_6$ have the same meaning as above, to yield a compound of formula (I/F), which is purified, if necessary, irrespective of the process according to which it has been obtained, which is separated, where appropriate, into its isomers and which is salified, if so desired, with a pharmaceutically acceptable acid or, where appropriate, with a pharmaceutically acceptable base, which compound of formula (I/F), when A represents a CO group, may be subjected, if so desired, to the action of an alkali metal mixed hydride to yield a compound of formula (I/F1):

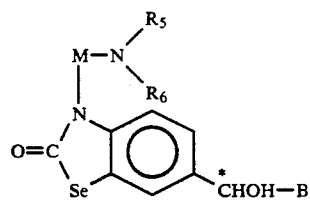

(I/F1)

in which A represents a CHOH group, M, $R_5$, $R_6$ and B having the same meaning as above, a special case of the compounds of formula (I) in which A represents a CHOH group and $R_2$ a lower alkyl group substituted with a group $NR_5R_6$ and $R_1$ forms a CO group with $R_4$, which is purified, if necessary, which is separated into its isomers, if so desired, and which is salified, if so desired, with a pharmaceutically acceptable acid or, where appropriate, with a pharmaceutically acceptable base, which compound of formula (I/A), (I/B), (I/C) or (I/D) is treated, if so desired:

either with an alkali metal hydroxide to yield a compound of formula (I/G):

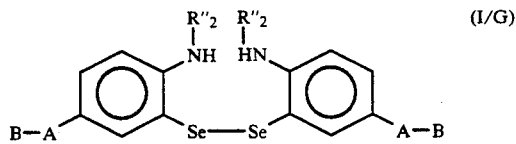

(I/G)

in which A, B and $R''_2$ have the same definition as above, a special case of the compounds of formula (I), or with an amine of formula $NR_7R_8$ in the presence of formaldehyde to yield a compound of formula (I/H):

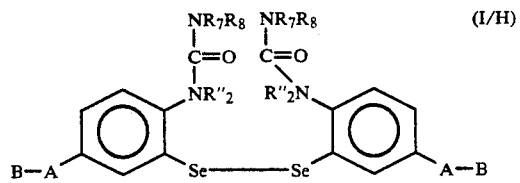

(I/H)

in which A, B, $R''_2$, $R_7$ and $R_8$ have the same definition as above, a special case of the compounds of formula (I), which compound of formula (I/G) or (I/H) is purified, if so desired, by a conventional technique of chromatography and/or crystallization, and which can, where appropriate, be separated into its isomers and, if so desired, salified, where appropriate with a pharmaceutically acceptable base or acid.

A special case of the compounds of the present invention consists of the compounds for which $R_2$ represents a methyl unit substituted with a group $NR_5R_6$ or an OH group and $R_1$ forms a C=O group with $R_4$. These compounds may be advantageously obtained in a lower aliphatic alcohol medium from a compound of formula (II), (I/A), (I/B), or (I/C) for which $R_2''$ represents a hydrogen atom, and by adding an excess of formaldehyde and heating the solution obtained to a temperature between room temperature and the boiling point of the solution, to yield, after cooling where appropriate, standing for one to two hours, filtration and, where appropriate, purification by chromatography and/or crystallization, a compound of formula (I/J):

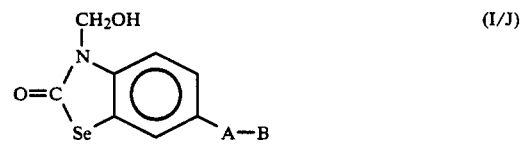

(I/J)

a special case of the compounds of formula (I) for which $R_2$ represents a $CH_2OH$ group, $R_1$ forms a CO group which $R_4$ and A and B have the same definition as in the formula (I), which maybe treated with a halogenating agent to yield a compound of formula (I/E1):

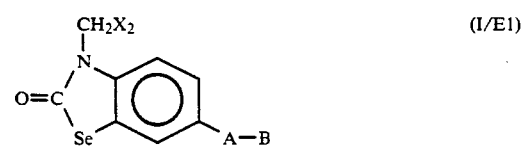

(I/E1)

in which $X_2$ represents a halogen atom and A and B have the same definition as in the formula (I), a special case of the compounds of formula (I/E) for which M represents a $CH_2$ group, which may be treated with an amine formula (VIII):

$$NR_5R_6 \quad (VIII)$$

in which $R_5$ and $R_6$ have the same definition as in the formula (I),
to yield a compound of formula (I/F1):

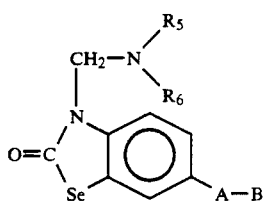

a special case of the compounds of formula (I/F) in which M represents a $CH_2$ group and A, B, $R_5$ and $R_6$ have the same definition as in the formula (I), which is purified, if necessary, the isomers of which are separated, where appropriate, and which is salified, if so desired, with a pharmaceutically acceptable acid or, where appropriate, base.

Another special case of the compounds of the present invention relates to the compounds for which B represents a styryl group or a substituted styryl group, A represents a CO group and $R_1$ forms a CO group with $R_4$. Such compounds will be advantageously obtained by reaction of a compound of formula (I/I):

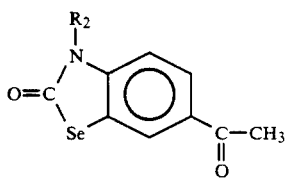

in which $R_2$ has the same definition as in the formula (I), with a benzaldehyde of formula (X):

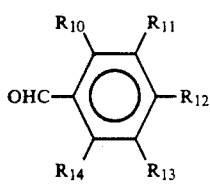

in which $R_{10}$, $R_{11}$ $R_{12}$, $R_{13}$ and $R_{14}$, which may be identical or different, represent, independently of one another, a hydrogen atom, a lower alkyl, lower alkoxy, hydroxyl, trifluoromethyl, carboxyl or amino group or halogen atoms,
to yield a compound of formula (I/S):

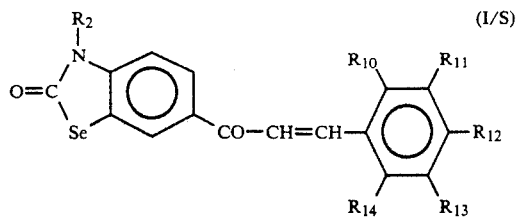

in which $R_2$, $R_{10}$, $R_{11}$, $R_{12}$, $R_{13}$ and $R_{14}$ have the same definition as above, which is purified by a technique of chromatography or crystallization, the isomers of which are separated, if so desired, and which is salified, where appropriate, with a pharmaceutically acceptable base or acid.

A pharmacological study of the compounds of the invention showed, in effect, that they were of low toxicity and endowed with a good level of anti-inflammatory analgesic activity and noteworthy anti-oxidant, antihypoxic, normolipemic, normogycemic, platelet aggregation-inhibitory and immunostimulatory properties. This spectrum of activity renders the compounds of the present invention advantageous in a number of indications, such as rheumatic pain and, very generally speaking, rheumatic diseases, lumbosciatic neuralgia, cervicobrachial neuralgia, pain associated with trauma such as sprains, fractures, dislocations, post-traumatic pain, postoperative pain, neurological pain such as facial neuralgia, and also the prevention of acute attacks of peripheral arterial and cerebrovascular ischemia, ischemic and anoxic hypoxic disorders and hence in the symptoms of defects of intellect, the pathology of the elderly, Alzheimer's disease, mnestic disorders, Parkinson's disease, attention disorders, in the prevention and treatment of platelet disorders, in hyperchloesterolemia, and hypertriglyceridemia, and in non-insulin dependent diabetes as well as its multifarious complications such as cataracts, visual disorders, neuropathies and nephropathies. As an immunostimulant, the products of the invention may be used in the treatment of certain forms of cancer. Their antioxidant property also enables them to be used as preservative, in particular for organs.

The subject of the present invention is also pharmaceutical compositions containing the products of formula (I) or one of their addition salts with a pharmaceutically acceptable base, alone or in combination with one or more pharmaceutically acceptable, non-toxic, inert excipients or vehicles.

Among the pharmaceutical compositions according to the invention, there maybe mentioned, more especially, those which are suitable for oral, parenteral or nasal administration, simple or sugar-coated tablets, sublingual tablets, sachets, packets, hard gelatin capsules, preparations to be dissolved under the tongue, troches, suppositories, creams, ointments, skin gels and organ preservation solutions.

The appropriate dosage varies according to the patient's age and weight, the administration route and the nature of the therapeutic indication or of any associated treatments, and ranges between 0.1 centigram and 4 grams per 24 hours.

The examples which follow illustrate the invention and in no way limit it.

The preparations do not form part of the invention. However, they constitute advantageous synthesis intermediates for obtaining the products of the invention.

Preparation 1

3-Methylbenzoselenazolinone 0.01 mol of benzoselenazolinone is introduced into a ground-necked round-bottomed flask containing 0.35 gram (0.015 gram-atom) of sodium dissolved in 50 l cm$^3$ of absolute alcohol. 3.1 cm$^3$ (0.05 mol) of methyl iodide are added dropwise and with stirring. After 12 hours, the solvent is evaporated off. The solid obtained is taken up with 30 to 40 cm$^3$ of water and then extracted with chloroform. The chloroform phase is dried over calcium chloride and the solvent is then evaporated off under reduced pressure. The product is recrystallized in cyclohexane.

Yield: 80%
Melting point: 57°-80° C.

Preparation 2

1-(2-Chloroethyl)-4-Arylpiperazines (hydrochloride)

0.048 mol of potassium carbonate and then 0.048 mol of 1-bromo-2-chloroethane are added to a solution of 0.04 mol of arylpiperazine in 40 cm$^3$ of dimethylformamide. The mixture is stirred at room temperature for 22 hours. The inorganic precipitate is drained and washed with dimethylformamide. The filtrate is acidified with sufficient absolute alcohol saturated with dry hydrochloric acid, and 300 to 400 cm$^3$ of anhydrous ether are then added. The precipitate of 1-(2-chloroethyl)-4-arylpiperazine hydrochloride is drained.

EXAMPLE 1

6-Benzoylbenzoselenazolinone 1.98 g (0.01 mol) of benzoselenazolinone, 50 to 60 g of polyphosphoric acid and 1.35 g (0.011 mol) of benzoic acid are introduced into a 100-cm$^3$ round-bottomed flask. The mixture is heated on an oil bath to a temperature of 130° C. for a time T of 3 hours, with stirring. The reaction mixture is then hydrolyzed in 300 cm$^3$ of cold water. The product is drained, washed with water, dried and recrystallized.

Recrystallization solvent: 95° strength ethanol
Yield: 70%
Melting point: 204° C.
Percentage composition: Calculated: C 55.64, H 3.00, N 4.63, Found: C55.25, H 3.00, N 4.63.

EXAMPLE 2

3-methyl-6-Benzyolbenzoselenazolinone 50 cm$^3$ of absolute alcohol, 0.35 g of sodium and then 2.8 g (0.1 mol) of 6-benzoylbenzoselenazolinone, obtained in Example 1, are introduced into a round-bottomed flask. 3.1 cm$^3$ (0.05 mol) of methyl iodide are added dropwise and with stirring. The mixture is left for twelve hours at room temperature. It is evaporated to dryness. The residue is taken up with 30 to 40 cm$^3$ of water. The product is drained, washed with water, dried and recrystallized.

Recrystallization solvent: 95° strength ethanol
Yield: 73%
Melting point: 156° C.
Percentage comosition: Calculated: C 56.97, H 3.49, N 4.42, Found: C 56.81, 1 H 3.50, N 4.32.

EXAMPLE 3

6Butyrylbenzoselenazolinone

Using the procedure described in Example 1 and replacing benzoic acid by butyric acid, the product of the title is obtained.

Heating temperature: 90°-95° C.
Heating time: 2 h 30 min
Recrystallization solvent: tolune/ethyl acetate, 8:2
Yield: 48%
Melting point: 166°-167° C.
Percentage composition:
Calculated: C 49.27, H 4.13, N 5.22, Found: C 48.86, H 4.13, N 5.12.

EXAMPLE 4

3-Methyl-6-butyrylbenzoselenazolinone

Using the procedure described in Example 2, but replacing 6-benzoylbenzoselenazolinone by 6-butyrylbenzoselenazolinone obtained in Example 3, the product of the title is inhibited.

Crystallization solvent: ethanol/water (4:1)
Yield: 70%
Melting point: 126°-127° C.
Percentage composition: Calculated: C 51.08, H 4.64, N 4.96, Found: C 51.05, H 4.91, N 4.96.

EXAMPLE 5

6-Acetylbenzoselenazolinone 12 grams (0.09 mol) of aluminum chloride are introduced into a ground-necked flask. 3.1 cm$^3$ (0.04 mol) of dimethylformamide are added dropwise with stirring. After cooling, two grams (0.01 mol) of benzoselenazolinone are added and the mixture is homogenized. It is heated to 70°-80° C. on an oil bath with stirring, and 0.01 to 0.012 mol of acetyl chloride is then added. heating is maintained at a temperature of 80°-90° C. for a time T of approximately 4 h 30 min. The mixture is hydrolyzed on crushed ice. The product is drained, dried, and washed with boiling cyclohexane and recrystallized in toluene.

Yield: 80%
Melting point: 185° C.
Percentage composition: Calculated: C 44.72, H 2.71, N 5.62, Found: C 45.02, H 2.94, N 5.83.

EXAMPLE 6

3-Methyl-6-Acetylbenzoselenazolinone

Using the procedure described in Example 2, but replacing 6-benzoylbenzoselenazolinone by 6-acetylbenzoselenazolinone obtained in Example 5, the product of the title is obtained.

Yield: 87%
Melting point: 132°-133° C.
Percentage composition: Calculated: C 47.26, H 3.57, N 5.51, Found: C 47.13, H 3.71, N 5.34.

EXAMPLE 7

3-Methyl-6-(3,5-Di-Tert-Butyl-4-Hydroxycinnamoyl)-benzoselenazolinone

In a 500 ml ground-necked flask equipped with a stirrer, 0.01 mol of 6-acetyl-3-methylbenzoselenazolinone is dissolved in 100 ml of ethanol saturated with hydrochloric acid.

0.01 mol of 3,5-di-tert-butyl-4-hydroxybenaldehyde is added slowly and with stirring. The reaction medium is left at room temperature for two hours. The reaction medium is poured into water and the precipitate is drained, washed with water until the filtrate is neutral and dried. The product is recrystallized.

Recrystallization solvent: 95° strength alcohol
Yield: 80%
Melting point: 203° C.
Percentage Composition Calculated: C 63.82, H 6.21, N 2.98, Found: C 63.48, H 6.20, N 3.08.

EXAMPLE 8

6-(3,5-Di-tert-butyl-4-hydroxycinnamoyl)benzoselenazolinone

The procedure is as described in Example 7, replacing 6-acetyl-3-methylbenzoselenazolinone by 6-acetylbenzoselenazolinone.

Recrystallization solvent: 95° strength alcohol
Yield: 75%
Melting point: 248°–249° C.
Percentage composition: Calculated: C 63.15, H 5.96, N 3.07, Found: C 62.95, H 5.66, N 3.24.

EXAMPLE 9

6-(4'-Chlorobenzoyl)benzoselenazolinone

Using the procedure described in Example 1, but replacing benzoic acid by 4-chlorobenzoic acid, the product of the title is obtained.

Heating time: 4 h
Heating temperature: 130° C.
Recrystallization solvent: 95° strength ethanol
Yield: 70%
Melting point: above 260° C.
Percentage composition:
Calculated: C 49.95, H 2.39, N 4.16, Found: C 50.52, H 2.57, N 4.17.

EXAMPLE 10

6-Nicotinoylbenzoselenazolinone 9.9 ml (0.13 mol) of dimethylformamide are introduced dropwise and with stirring into a 250-ml flask containing 61.3 g (0.46 mol) of aluminum chloride, and the flask is fitted with a reflux condenser and heated in an oil bath to a temperature in the region of 45° C. 7.9 g (0.04 mol) of benzoselenazolinone and 10.6 g (0.06 mol) of nicotinoyl chloride hydrochloride are introduced.

The reaction mixture is heated to a temperature of 100° C. for a time T (8 hours). It is poured into a sufficient quantity of ice, the resulting mixture is stirred for one hour and the precipitate formed is drained, washed with water and dried. The product is recrystallized in ethanol.

Yield: 50%
Melting point: 210° C. (decomposition)
Percentage composition: Calculated: C 51.50, H 2.66, N 9.24, Found: C 51.04, H 2.62, N 9.07.

EXAMPLE 11

3-Methyl-6(4-Chlorobenzoyl)benzoselenazolinone 0.35 gram (0.015 gram-atom) of sodium dissolved in 50 cm³ of absolute alcohol and 3.40 g (0.01 mol) of 6-(4-chlorobenzoyl)benzoselenazolinone, obtained in Example 9, are introduced into a ground-necked round-bottomed flask. 3.1 cm³ (0.05 mol) of methyl iodide are then added dropwise and with stirring. After 12 hours, the solvent is evaporated off. The solid obtained is taken up with 30 to 40 cm³ of water and the mixture is extracted with chloroform. The chloroform phase is dried over calcium chloride and the solvent is then evaporated off under reduced pressure. The product is recrystallized in 95° strength alcohol.

Yield: 65%
Melting point: 180° C. (decomposition)
Percentage composition: Calculated: C 51.38, H 2.87, N 3.99, Found: C 51.43, H 2.75, N4.06.

EXAMPLE 12

3-Methyl-6-Nicotinoylbenzoselenazolinone

Using the procedure described in Example 5, but replacing benzoselenazolinone by 3-methylbenzoselenazolinone obtained in Preparation 1 and acetyl chloride by nicotinoyl chloride, the product of the title is obtained.

Heating time: 10 to 12 hours
Heating temperature: 90° C.
Recrystallization solvent: 95° strength ethanol
Yield: 60%
Melting point: 157° C.
Percentage composition: Calculated: C 53.01, H 3.18, N 8.83, Found: C 52.50, H 3.29, N 9.03.

EXAMPLE 13

3-Methyl-6-Furoylbenzoselenazolinone

Using the procedure described in Example 10, but replacing nicotinoyl chloride hydrochloride by 2-furoyl chloride, the product of the title is obtained.

Spectral characteristics: 1680 cm$^{-1}$ $\nu$CO SeCON 1650 cm$^{-1}$ $\nu$CO

EXAMPLE 14

4-Oxo-4-(2-Oxobenzoselenazolin-6-yl)butyric Acid 8.6 ml (0.115 mol) of dimethylformamide are introduced dropwise and with stirring into a 250-ml flask containing 53.3 g (0.4 mol) of aluminum chloride. The flask is equipped with a reflux condenser and heated on an oil bath to a temperature in the region of 45° C. 5.4 g (0.04 mol) of benzoxazolinone and 6 g of succinic anhydride (0.06 mol) are introduced. The reaction mixture is heated to 95° C. for 5 hours. It is poured into a sufficient quantity of ice, the resulting mixture is stirred for one hour and the precipitate formed is drained.

The product obtained is taken up with 10% aqueous sodium bicarbonate solution. The alkaline solution is extracted several times with ether and the aqueous phase is then acidified with dilute hydrochloric acid. The precipitate obtained is drained, washed with water and dried and recrystallized.

Spectral characteristics: 3300 cm$^{-1}$ $\nu$OH (acid) 1730 cm$^{-1}$ $\nu$CO (acid) 1670 cm$^{-1}$ $\nu$CO (SeCON) 1600 cm$^{-1}$ $\nu$C=C (aromatic)

EXAMPLE 15

4-Oxo-4-(2-Oxobenzoselenazolin-6-yl)buten-2-oic Acid

Using the procedure described in Example 14, but replacing succinic anhydride by maleic anhydride, the product of the title is obtained.

Spectral characteristics: 3280 cm$^{-1}$ m OH (acid) 1670 cm$^{-1}$ m CO (SeCON) 1720 cm$^{-1}$ m CO (acid)

EXAMPLE 16

2-Methylene-4-Oxo-4-(2-Oxobenzoseslenazolin-6-yl)Butyric Acid

Using the procedure described in Example 14, but replacing succinic anhydride by itaconic anhydride, the product of the title is obtained.

Spectral characteristics:
Infrared: 1670 cm$^{-1}$ m CO (SeCON)

EXAMPLE 17

2-(2-Oxobenzoselenazolin-6-ylcarbonyl)benzoic Acid

Using the procedure described in Example 14, but replacing succinic anhydride by phthalic anhydride, the product of the title is obtained.

Spectral characteristics: Infrared: 3460 cm$^{-1}$ m OH 1670 cm$^{-1}$ m CO (SeCON)

EXAMPLE 18

6-Isonicotinoylbenzoselenazolinone

Using the procedure described in Example 10, but replacing nicotinoyl chloride hydrochloride by isonicotinoyl chloride hydrochloride, the product of the title is obtained.

EXAMPLE 19

6-(3-Quinolylcarbonyl)benzoselenazolinone

Using the procedure described in Example 10, but replacing nicotinoyl chloride hydrochloride by 3-quinolinecarbonyl chloride hydrochloride, the product of the title is obtained.

EXAMPLE 20

3-(2-Chloroethyl)Benzoselenazolinone 0.06 mol of potassium carbonate and then 0.015 mol of 1-bromo-2-chloroethane are added to a solution of 0.015 mol of benzoselenazolinone in 30 cm$^3$ of dimethylformamide. The mixture is heated to 50° C. with stirring for six hours. The inorganic precipitate is drained and then washed with dimethyl formamide. The DMF is evaporated off under reduced pressure and the residue is taken up with water. An extraction with ether is then carried out. The organic phase is dried over sodium sulfate and then filtered. The ether phase is evaporated to dryness under reduced pressure and the product is recrystallized in petroleum ether.

Yield: 50%
Melting point: 55° C.
Percentage composition: Calculated: C 41.48, H 3.09, N 5.37, Found: C 41.61, H 2.66, N 5.42.

Spectral Characteristics: Infrared: 1650 cm$^{-1}$: λCO
Nuclear magnetic Resonance, ($^1$H) CDCl$_3$ δ:3.75 ppm, doublet of triplet 2H, CH$_2$—N δ:4.25 ppm, doublet of triplet 2H, CH$_2$—Cl

EXAMPLE 21

3-(3-Chloropropyl)benzoselenazolinone

Using the procedure described in Example 20, but replacing 1-bromo-2-chloroethane by 1-bromo-3-chloropropane, the product of the title is obtained.

Yield: 50%
Melting point: 51° C.
Percentage composition: Calculated: C 43.74, H 3.67, N 5.10, Cl 12.91, Found: C 43.69, H 3.64, N 5.09, Cl 12.05.

Spectral characteristics: Infrared: 1750 cm$^{-1}$: ν(CH Ar); 1640 cm$^{-1}$ν(CO); 2900-2990 cm$^{-1}$ ν(CH$_2$)

Nuclear Magnetic Resonance, ($^1$H) CDCl$_3$ δ:2.25 ppm, 2H, N—CH$_2$ δ:3.60 ppm, quadruplet, CH$_2$—CH$_2$—CH$_2$ δ:4.10 ppm, triplet 2H—CH$_2$—Cl

EXAMPLE 22

3-[2-(4-Phenyl-1-Piperazinyl)ethyl]benzoselenazolinone (Hydrochloride)

Procedure 1

2 g (0.01 mol) of benzoselenazolinone, 2.62 g (0.01 mol) of 1-(2-chloroethyl)-4-phenylpiperazine (hydrochloride) and 5.52 g (0.04 ml) of potassium carbonate are introduced together with 30 cm$^3$ of dimethylformamide into a ground-necked flask. The mixture is heated to 50° C. with stirring for twenty hours and then drained. The filtrate is recovered under reduced pressure and the residue is taken up with water. The product is extracted with chloroform. The organic phase is recovered, dried over sodium sulfate, filtered and concentrated, a stream of gaseous hydrochloric acid is bubbled through it and it is evaporated to dryness. The product is recrystallized.

Recrystallization solvent: dioxane
Yield: 50%
Melting point: 234° C.
Percentage composition: Calculated: C 53.97, H 5.24, N 9.94; Cl 8.38, Found: C 53.90, H 5.36, N 10.00, Cl 8.40.

Spectral characteristics: Infrared: 1650 cm$^{-1}$: ν(Se CON) 1450 cm$^{-1}$: νCH$_3$—N Nuclear Magnetic Resonance, ($^1$H) CDCl$_3$ δ:2.90-4.00 ppm, unresolved peaks, 10H piperazine CH$_3$—N δ:4.50 ppm, triplet, 2H benzoselenazolinone CH$_2$—N

PROCEDURE 2

This compound may also be obtained according to the following procedure:

0.01 mol of 3-(2-chloroethyl)benzoselenazolinone, obtained in Example 20, one equivalent of 1-phenylpiperazine and 0.04 mol of potassium carbonate in 30 cm$^3$ of dimethylformamide are placed in around-bottomed flask placed under argon and surmounted by a condenser. The mixture is heated to 50° C. with stirring for eight hours and then drained. The filtrate is evaporated under reduced pressure and the residue is taken up with ethyl ether. The organic phase is dried over sodium sulfate, filtered and concentrated. The mixture is left for crystallization to take place. The product is drained and washed with ether.

EXAMPLE 23

3-{2-[4-(3-Trifluoromethylphenyl)-1-piperazinyl]ethyl}-benzoselenazolinone

Using the procedure described in Example 22, procedure 2, but replacing 1-phenylpiperazine by 1-(3trifluoromethylphenyl)piperazine, the product of the title is obtained.

EXAMPLE 24

3-{2-[4-(2-Methoxyphenyl)-1-piperazinyl]ethyl}benzoselenazolinone

Using the procedure described in Example 22, procedure 2, but replacing 1-phenylpiperazine by 1-(2- methoxyphenyl)piperazine, the product of the title is obtained.

EXAMPLE 25

3-{2-[4-(4-Fluorophenyl)-1-piperazinyl]ethyl}benzoselenazolinone

Using the procedure described in Example 22, procedure 2, but replacing 1-phenylpiperazine by 1-(4-fluorophenyl)piperazine, the product of the title is obtained.

EXAMPLE 26

3-[2-(1-Pyrrolidinyl)ethyl]benzoselenazolinone

Using the procedure described in Example 22, procedure 2, but replacing 1-phenylpiperazine by pyrrolidine, the product of the title is obtained.

EXAMPLE 27

3(2-Morpholinoethyl)benzoselenazolinone

Using the procedure described in Example 22, procedure 2, but replacing 1-phenylpiperazine by morpholine, the product of the title is obtained.

Yield: 65%

Melting point: 80° C.

Percentage composition: Calculated: C 50.17, H 5.18, N 9.00, Found: C 50.21, H 5.24, N 9.07.

Spectral characteristics:

Infrared: 2990–2790 cm$^{-1}$ $\nu$CH (CH$_2$CH$_2$) 1660 cm$^{-1}$ $\nu$CO (NCOSe) 1110 cm$^{-1}$ $\nu$CO (CH$_2$—O—CH$_2$)

Nuclear Magnetic Resonance: $\delta$=7.00 to 7.60 ppm, 4H, unresolved peaks, aromatic $\delta$=4.10 ppm, 2H, triplet, N—CH$_2$—CH$_2$-morpholine $\delta$=3.60 ppm, 4H, unresolved peaks, 2(CH$_2$—O) $\delta$=2.50 ppm, 6H, unresolved peaks, morpholine CH$_2$N(CH$_2$)$_2$

EXAMPLE 28

3-(2-Dimethylaminoethyl)benzoselenazolinone (Hydrochloride)

Using the procedure described in Example 22, procedure 1, but replacing 1-(2-chloroethyl)-4phenylpiperazine (hydrochloride) by 1-chloro-2-dimethylaminoethane hydrochloride, the product of the title is obtained.

Recrystallization solvent: absolute ethanol

Yield: 55%

Melting point: 232° C.

Percentage composition: Calculated: C 43.25, H 4.95, N 9.17, Cl 11.60, Found: C 43.03, H 5.00, N 9.11, Cl 11.48.

Infrared Spectrometry:

1650 cm$^{-1}$$\nu$CO SeCON

Nuclear Magnetic Resonance Spectrometry, $\delta$=2.30 ppm, singlet, 6H, 2CH$_3$

EXAMPLES 29 to 34

Using the procedure described in Examples 22 (procedure 2) and 27 to 28, but replacing 3-(2-chloroethyl)-benzoselenazolinone by 3-(3-chloropropyl)benzoselenazolinone, the following are obtained:

EXAMPLE 29

3-[3-(4-Phenyl-1-Piperazinyl)propyl]benzoselenazolinone

EXAMPLE 30

3-{3-[4-(3-Trifluoromethylphenyl)-1-piperazinyl]-propyl}-benzoselenazolinone

EXAMPLE 31

3-{3-[4-(4-Fluorophenyl)-1-piperazinyl]propyl}benzoselenazolinone

EXAMPLE 32

3-[3-(1-Pyrrolidinyl)propyl]benzoselenazolinone

EXAMPLE 33

3-(3-Morpholinopropyl)benzoselenazolinone

EXAMPLE 34

3-(3-Dimethylalminopropyl)benzoselenazolinone

EXAMPLE 35

3-(Hydroxymethyl)benzoselenazolinone 2 grams (0.01 mol) of benzoselenazoline, 2 cm$^3$ (0.02 mol) of aqueous formaldehyde solution and 2 cm$^3$ of methanol are introduced into a ground-necked flask. The mixture is brought to reflux two hours. After cooling to 40° C. 20 cm$^3$ of water are added. The mixture is allowed to cool and the product is drained, washed with water, dried and recrystallized in cyclohexane.

Yield: 85%

Melting point: 105°–106° C.

Percentage composition: Calculated: C 42.12, H 3.09, N 6.14, Found: C 42.42, H 3.33, N 6.08.

Spectral characteristics: Infrared: 1660 cm$^{-1}$ $\nu$CO $^1$H Nuclear Magnetic Resonance, DMSO-d$_5$ $\delta$=5.30 ppm, doublet, 2H, CH$_2$OH

EXAMPLE 36

3-(Bromomethyl)benzoselenazolinone

A stream of gaseous hydrobromic acid is bubbled with stirring into a round-bottomed flask containing 0.02 mol of 3-(hydroxymethyl)benzoselenazolinone dissolved in acetone. The mixture is filtered. The product is recrystallized in cyclohexane.

Yield: 50%

Melting point: 124° C.

Spectral characteristics:

Infrared:

1660 cm$^{-1}$$\nu$ CO $^1$H Nuclear Magnetic Resonance: CDCl$_3$ $\delta$=5.70 ppm, doublet, 2H, CH$_2$Br

EXAMPLE 37

3-(Chloromethyl)benzoselenazolinone 0.55 cm$^3$ of thionyl chloride (0.02 mol) is added dropwise and with stirring into a round-bottom flask containing 0.01 mol of 3-(hydroxymethyl)benzoselenazolinone dissolved in 100 cm$^3$ of chloroform. The mixture is brought to reflux for 2 hours and the chloroform is then evaporated off under reduced pressure. The product is recrystallized in cyclohexane.

Yield: 80%

Melting point: 97°–98° C.

Spectral characteristics: Infrared: 1660 cm$^{-1}$$\nu$CO $^1$H Nuclear Magnetic Resonance: $\delta$=5.70 ppm, doublet, 2H, CH$_2$Cl

EXAMPLE 38

3-[(4-Phenyl-1-piperazinyl)methyl]benzoselenazolinone (Hydrochloride)

The procedure is as described in Example 22, procedure 2, replacing 3-(2-bromethyl)benzoselenazolinone by 3-(bromomethyl)(benzoselenazolinone. After the residue has been taken with ethyl ether, a stream of gaseous hydrochloric acid is bubbled through, the mixture is evaporated to dryness and the product is recrystallized.

Spectral characterististics: Infrared: 1650 cm$^{-1}$ $\nu$CO (SeCON)

EXAMPLE 39

3-[4-(3-Trifluoromethylphenyl)-1-piperazinylmethyl]-benzoselenazolinone

Using the procedure described in Example 38, but replacing 1phenylpiperazine by 1-(3-trifluoromethylphenyl)piperazine, the product of the title is obtained.

EXAMPLE 40

3-[4-(2-Methoxyphenyl)-1-piperazinylmethyl]benzoselenazolinone

Using the procedure described in Example 38, but replacing 1-phenylpiperazine by 1-(2-methoxyphenyl)-piperazine, the product of the title is obtained.

EXAMPLE 41

3-[4(4-Fluorophenyl)-1-Piperazinylmethyl]benzoselenazolinone

Using the procedure described in Example 38, but replacing 1-phenylpiperazine by 1-(4-fluorophenyl)piperazine, the product of the title is obtained.

EXAMPLE 42

3-(1Pyrrolidinylmethyl)benzoselenazolinone

Using the procedure described in Example 38, but replacing 1-phenylpiperazine by pyrrolidine, the product of the title is obtained.

EXAMPLE 43

3-(Morpholinomethyl)benzoselenazolinone

Using the procedure described in Example 38, but replacing 1-phenylpiperazine by morpholine, the product of the title is obtained.

EXAMPLE 44

3-(Dimethylaminomethyl)benzoselenazolinone

Using the procedure described in Example 38, but replacing 1-phenylpiperazine by dimethylamine, the product of the title is obtained.

EXAMPLE 45

3-(2-Isopropylaminoethyl)benzoselenazolinone (Hydrochloride)

Using the procedure described in Example 22, but replacing 1-phenylpiperazine by isopropylamine, the product of the title is obtained. After the residue has been taken up with ethyl ether, a stream of gaseous hydrochloric acid is bubbled through, the mixture is evaporated to dryness and the product is recrystallized.

EXAMPLE 46

3-(2-Naphthylaminoethyl)benzoselenazolinone using the procedure described in Example 22 (procedure 2), but replacing 1-phenylpiperazine by naphthylamine, the product of the title is obtained.

EXAMPLE 47

3-(2-Benzylaminomethyl)benzoselenazolinone (Hydrochloride)

Using the procedure described in Example 22 (procedure 2), but replacing 1-phenylpiperazine by benzylamine, the product of the title is obtained. After the residue has been taken up with ethyl ether, a stream of gaseous hydrochloric acid is passed through, the mixture is evaporated to dryness and the product is recrystallized.

EXAMPLE 48

3-[2-(2-Chlorophenyl)aminoethyl]benzoselenazolinone (Hydrochloride)

Using the procedure described in Example 22 (procedure 2), but replacing 1-phenylpiperazine by 4-chlorophenylamine, the product of the title is obtained. After the residue has been taken up with ethyl ether, a stream of gaseous hydrochloric acid is bubbled through, the mixture is evaporated to dryness and the product is recrystallized.

EXAMPLE 49

3-[2-(8-Amino-1-naphthyl)aminoethyl]benzoselenazolinone

Using the procedure described in Example 22 (procedure 2), but replacing 1-phenylpiperazine by 1,8-diaminonaphthalene, the product of the title is obtained. After the residue has been taken up with ethyl ether, a stream of gaseous hydrochloric acid is bubbled through, the mixture is evaporated to dryness and the product is recrystallized.

EXAMPLE 50

3-[2-(3-Amino-2-naphthyl)aminoethyl]benzoselenazolinone

Using the procedure described in Example 22 (procedure 2), but replacing 1-phenylpiperazine by 2,3-diaminonaphthalene, the product of the title is obtained. After the residue has been taken up with ethyl ether, a stream of gaseous hydrochloric acid is bubbled through, the mixture is evaporated to dryness and the product is crystallized.

EXAMPLE 51

3-METHYL-6-[PHENYL(HYDROXY)METHYL]-BENZOSELENAZOLINONE 0.01 mol of 3-methyl-6-benzoylbenzoselenazolinone, obtained in Example 2, in 50 cm$^3$ of methanol is placed in a flask. The mixture is heated gently and 0.1 mol of sodium borohydride is added gradually. The mixture is left stirring for 12 hours. The reaction medium is evaporated on a water bath under vacuum. The residue is washed with water. It is dried. The product is recrystallized.

EXAMPLE 52

3-METHYL-6-(1-HYDROXYBUTYL)BENZOSELENAZOLINONE

Using the procedure described in Example 51, but replacing 3-methyl-6-benzoylbenzoselenazolinone by 3-methyl-6-butyrylbenzoselenazolinone, obtained in Example 4, the product of the title is obtained.

EXAMPLE 53

3-METHYL-6-(1-HYDROXYETHYL)BENZOSELENAZOLINONE

Using the procedure described in Example 51, but replacing 3-methyl-6-benzoylbenzoselenazolinone by 3-methyl-6-acetylbenzoselenazolinone, obtained in Example 6, the product of the title is obtained.

EXAMPLE 54

6-(CYCLOHEXYLCARBONYL)BENZOSELENAZOLINONE

Using the procedure described in Example 1, but replacing benzoic acid by cyclohexanecarboxylic acid, the product of the title is obtained.

EXAMPLE 55

6-(6-METHYLNICOTINOYL)BENZOSELENAZOLINONE

Using the procedure described in Example 10, but replacing nicotinoyl chloride by 6-methyl nicotinoyl chloride, the product of the title is obtained.

EXAMPLE 56

6-(PHENYLACETYL)BENZOSELENAZOLINONE

Using the procedure described in Example 1, but replacing benzoic acid by phenylacetic acid, the product of the title is obtained.

EXAMPLE 57

3-(2-CHLOROETHYL)-6-BENZOYLBENZOSELENAZOLINONE

Using the procedure described in Example 20, but replacing benzoselenazolinone by 6-benzoylbenzoselenazolinone, the product of the title is obtained.

EXAMPLES 58 TO 63

Using the procedure described in Examples 22 (procedure 2) and 23 to 28, but replacing 3-(2-chloroethyl)benzoselenazolinone by 6-benzoyl-3-(2-chloroethyl)benzoselenazolinone, the following are obtained:

EXAMPLE 58

3-[2-(4-PHENYL-1-PIPERAZINYL)ETHYL]-6-BENZOYLBENZOSELENAZOLINONE

EXAMPLE 59

3-{2-[4-(3-TRIFLUOROMETHYLPHENYL)-1-PIPERAZINYL]ETHYL}-6BENZOYLBENZOSELENAZOLINONE

EXAMPLE 60

3-{2-[4-(4-FLUOROPHENYL)-1-PIPERAZINYL]ETHYL}-6-BENZOYLBENZOSELENAZOLINONE

EXAMPLE 61

3-[2-(1-PYRROLIDINYL)ETHYL]-6-BENZOYLBENZOSELENAZOLINONE

EXAMPLE 62

3-(2-MORPHOLINOETHYL)-6-BENZOYLBENZOSELENAZOLINONE

EXAMPLE 63

3-(2-DIMETHYLAMINOETHYL)-6-BENZOYLBENZOSELENAZOLINONE

EXAMPLE 64

BIS[2-(3,3-DIMETHYLUREIDO)PHENYL] DISELENIDE

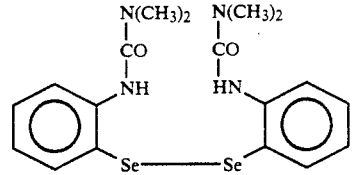

0.01 mol of benzoselenazolinone is introduced together with 18 cm³ of a 40% solution of dimethylamine (0.015 mol) into a 50-cm³ ground-necked flask. The mixture is stirred at room temperature and 0.011 mol of formaldehyde is then added. After two hours, 1 cm³ of 95° strength alcohol is added and the mixture is brought to reflux for 12 hours with stirring. After cooling, 1 to 3 cm³ of 95° strength alcohol is added and stirring is maintained for one month. The product is purified by flash chromatography on a column of silica gel (eluent:-chloroform/ethyl acetate, 8:2, to remove the impurities, then methanol to obtain the product). The product is recrystallized in ethyl ether.

Yield: 50%

Melting point: 116° C.

Percentage composition: Calculated: C 44.64, H 4.58, N 11.57, Found: C 44.60, H 4.51, N 11.29.

EXAMPLE 65

BIS(2-AMINO-5-BENZOYLPHENYL) DISELENIDE

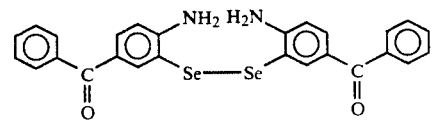

1.5 g (0.005 mol) of 6-benzoylbenzoselenazolinone are introduced together with 20 cm³ of 10% sodium hydroxide into a ground-necked flask. The mixture is heated to reflux with stirring for two hours. After cooling, the reaction medium is neutralized. The precipitate is drained, washed with water and dried and the product is recrystallized in toluene.

Yield: 80%

Melting point: 190° C.

Percentage composition: Calculated: C 56.74, H 3.66, N 5.09, Found: C 56.57, H 3.56, N 5.02.

EXAMPLE 66

BIS(2-METHYLAMINO-5-BENZOYLPHENYL) DISELENIDE

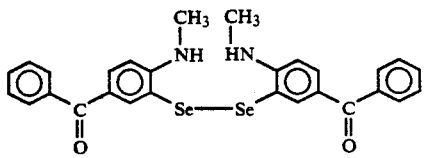

Using the procedure described in Example 65, but replacing 6-benzoylbenzoselenazolinone by 3-methyl-6-benzoylbenzoselenazolinone, the product of the title is obtained.

Recrystallization solvent: absolute alcohol

Yield: 60%

Melting point: 199°-200° C.

Percentage composition: Calculated: C 58.14, H 4.18, N 4.84, Found: C 57.97, H 4.24, N 4.89.

Spectral characteristics: Infrared 1625 cm$^{-1}$: $\nu$ CO (benzoyl) 3310–3320 cm$^{-1}$: $\nu$ NH$_2$ Nuclear Magnetic Resonance, ($^1$H) (CD$_3$)$_2$SO $\delta$: 2.85 ppm, doublet 6H, CH$_3$

EXAMPLE 67

BIS(2-AMINO-5-ACETYLPHENYL) DISELENIDE

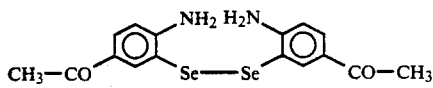

Using the procedure described in Example 65, but replacing 6-benzoylbenzoselenazolinone by 6-acetylbenzoselenazolinone, the product of the title is obtained.

Recrystallization solvent: acetone

Yield: 40%

Melting point: 238° C.

Spectral characteristics: Infrared: 1645 cm$^{-1}$: $\nu$ CO (acetyl) 3450 cm$^{-1}$: $\nu$ NH$_2$ Nuclear Magnetic Resonance: ($^1$H) (CD$_3$)$_2$SO $\delta$: 2.20 ppm, singlet 6H, CH$_3$

EXAMPLE 68

BIS[2-(3,3-DIMETHYLUREIDO)-5-BENZOYLPHENYL] DISELENIDE

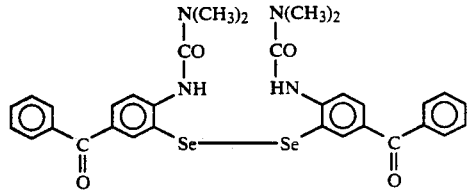

3 g (0.01 mol) of 6-benzoylbenzoselenazolinone are introduced together with 1.8 cm$^3$ (0.015 mol) of a 40% aqueous solution of dimethylamine and 5 cm$^3$ of 95° strength alcohol into a 50-cm$^3$ ground-necked flask. The constituents are mixed for a few minutes and 1 cm$^3$(0.011 mol) of 37% aqueous formaldehyde solution is then added. The mixture is stirred for 2 hours at room temperature and then heated to 80° C. for 15 hours. After cooling, the precipitate formed spontaneously is drained. 1.2 cm$^3$ dimethylamine are added to the filtrate and the mixture is brought to reflux with stirring for 9 hours. After cooling, the precipitate formed spontaneously is drained. The two precipitates are combined and the product to be obtained is purified by chromatography on a column of silica gel, using a 4:2 chloroform-/ethyl acetate mixture as elution solvent.

Yield: 50%

Melting point: 194°-195° C.

Percentage composition: Calculated: C 55.50, H 4.37, N 8.09, Found: C 55.37, H 4.09, N 7.98.

Spectral characteristics: Infrared 1625 cm$^{-1}$: $\nu$ CO (benzoyl) 1680 cm$^{-1}$: $\nu$ CO (carbamoyl) 3250 cm$^{-1}$: $\nu$ CO (NHCO)

Nuclear Magnetic Resonance: ($^1$H) (CD$_3$)$_2$SO $\delta$: 2.85 ppm, singlet 12H, CH$_3$

EXAMPLE 69

BIS[2-(3,3-DICYCLOHEXYLUREIDO)PHENYL] DISELENIDE

Using the procedure described in Example 64, but replacing dimethylamine by dicyclohexylamine, the product of the title is obtained.

EXAMPLE 70

BIS{2-[3(4-TRIFLUOROMETHYLBENZYL-)UREIDO]PHENYL} DISELENIDE

Using the procedure described in Example 64, but replacing dimethylamine by 4-trifluoromethylbenzylamine, the product of the title is obtained.

EXAMPLE 71

BIS[2-(3-METHYL-3-BENZYLUREIDO)PHENYL ] DISELENIDE

Using the procedure described in Example 64, but replacing dimethylamine by N-methyl-N-benzylamine, the product of the title is obtained.

EXAMPLE 72

BIS{2-[3-(4-CHLOROPHENYL)UREIDO]-PHENYL} DISELENIDE

Using the procedure described in Example 64, but replacing dimethylamine by 4-chloroaniline, the product of the title is obtained.

EXAMPLE 73

BIS[2-(MORPHOLINOCARBONYLAMINO)PHENYL] DISELENIDE

Using the procedure described in Example 64, but replacing dimethylamine by morpholine, the product of the title is obtained.

EXAMPLE 74

6-ETHYLBENZOSELENAZOLINONE 0.01 mol of 6-acetylbenzoselenazolinone, obtained in Example 5, and 20 cm$^3$ (0.27 mol) of trifluoracetic acid are weighed into a 100-cm³ ground-necked flask. 5.5 cm³ (0.022 mol) of triethylsilane are added dropwise and with magnetic stirring via a dropping funnel equipped with a Teflon tap, while cooling by means of a bath of ice-cold water. Stirring of the reaction medium is continued for 30 hours at room temperature. The reaction mixture is poured with stirring into one liter of ice-cold water. The precipitate obtained is drained and washed with water until the washing liquors are neutral. The product is dried. It is recrystallized in cyclohexane.

Yield: 80%
Melting point: 128° C. (decomposition)
Percentage composition: Calculated: C 47.80, H 4.01, N 6.19, Found: C 48.20, H 4.06, N 6.21.
Infrared Spectrometry: 1660 cm$^{-1}$ $\nu$ CO (SeCON)
Nuclear Magnetic Resonance Spectrometry: (CDCl$_3$) $\delta$: 1.25 ppm, triplet, 3H, CH$_3$ $\delta$: 2.5 ppm, quadruplet, 2H, CH$_2$

EXAMPLE 75

3-METHYL-6-ETHYLBENZOSELENAZOLINONE

Using the procedure described in Example 74, but replacing 6-acetylbenzoselenazolinone by 3-methyl-6-acetylbenzoselenazolinone, the product of the title is obtained.

EXAMPLE 76

6-BENZYLBENZOSELENAZOLINONE

Using the procedure described in Example 74, but replacing 6-acetylbenzoselenazolinone by 6-benzoylbenzoselenazolinone, the product of the title is obtained.

Yield: 95%
Melting point: 125°–127° C.
Percentage composition: Calculated: C 58.34, H 3.85, N 4.86, Found: C 58.62, H 3.87, N 4.80.
Infrared Spectrometry: 1640 cm$^{-1}$ $\nu$ CO (SeCON)
Nuclear Magnetic Resonance Spectrometry: (CDCl$_3$) $\delta$: 4.00 ppm, singlet, 2H, CH$_2$ $\delta$: 7.00 to 7.25 ppm, unresolved peaks, 8H, aromatic.

EXAMPLE 77

6(1-HYDROXYETHYL)BENZOSELENAZOLINONE 1.2 g (0.005 mol) of 6-acetylbenzoselenazolinone are introduced together with 7.5 cm³ of 3% sodium hydroxide into a ground-necked round-bottom flask cooled in an ice bath. 0.38 g (0.001 mol) of sodium borohydride is then added slowly and with stirring. The solution is stirred at room temperature for 15 hours an the acidified with aqueous hydrochloric acid solution diluted 4-fold. The precipitate obtained is drained, washed with water and then recrystallized in a mixture of cyclohexane (¼) and ethyl acetate (¾).

Yield: 80%
Melting point: 171° C.
Percentage composition: Calculated: C 44.64, H 3.75, N 5.78, Found: C 44.91, H 3.86, N 6.03.
Infrared Spectrometry: 1660 cm$^{-1}$ $\nu$ CO 3400 cm$^{-1}$ $\nu$ OH
Nuclear Magnetic Resonance Spectrometry: $^1$H, DMSO $\delta$: 1.25 ppm, doublet, 3H, CH$_3$ $\delta$: 4.65 ppm, doublet of double, CHOH

EXAMPLE 78

6-[PHENYL(HYDROXY)METHYL]BENZOSELENAZOLINONE

PROCEDURE 6 g (0.0198 mol) of 6-benzoylbenzoselenazolinone are introduced together with 30 cm³ of 3% sodium hydroxide into a ground-necked round-bottomed flask cooled in an ice bath. 1.14 g (0.030 mol) of sodium borohydride are then added slowly and with stirring. The solution is stirred at room temperature for 6 hours and then acidified with dilute aqueous hydrochloric acid solution diluted 4-fold. The precipitate obtained is drained, washed with water, dried and then recrystallized in a mixture of cyclohexane (⅓) and ethyl acetate (⅔).

Yield: 80%
Melting point: 126° C.
Percentage composition: Calculated: C 55.28, H 3.64, N 4.60, Found: C 55.11, H 3.77, N 4.55.
Infrared spectrometry: 1675 cm$^{-1}$ $\nu$ CO
Nuclear Magnetic Resonance Spectrometry: $^1$H, DMSO $\delta$: 5.60 ppm, singlet, 1H, CHOH

EXAMPLE 79

BIS[2-AMINO-5-(4-CHLOROBENZOYL)PHENYL] DISELENIDE

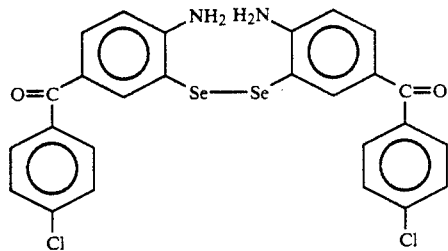

Using the procedure described in Example 65, but replacing 6-benzoylbenzoselenazolinone by 6-(4-chlorobenzoyl)benzoselenazolinone, the product of the title is obtained.

Recrystallization solvent: isopropanol
Yield: 60%
Melting point: 191° C.
Percentage composition: Calculated: C 50.43, H 2.93, N 4.52, Cl 11.45, Found: C 50.66, H 2.98, N 4.51, Cl 11.29.
Spectral characteristics Infrared 1600 cm$^{-1}$ $\nu$ CO para-chlorobenzoyl
Nuclear Magnetic Resonance Spectrometry: $^1$H, (CD$_3$)$_2$SO $\delta$: 6.57 ppm, singlet, 4H, broad peak, NH$_2$ $\delta$: 6.83 ppm, doublet, 2H, H$_3$ and 3'

EXAMPLE 80

BIS(2-AMINO-5-BENZYLPHENYL) DISELENIDE

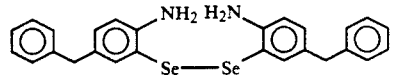

Using the procedure described in Example 65, but replacing 6-benzoylbenzoselenazolinone by 6-benzylbenzoselenazolinone, the product of the title is obtained.

Recrystallization solvent: 95° ethanol
Yield: 70%
Melting point: 101° C.
Percent composition: Calculated: C 59.78, H 4.63, N 5.36, Found: C 59.80, H 4.56, N 5.37.
Spectral characteristics Infrared 3280 cm$^{-1}$, 3380 cm$^{-1}$ ν NH
Nuclear Magnetic Resonance: $^1$H, (CD$_3$)$_2$SO δ: 3.76 ppm, singlet, 4H, CH$_2$

EXAMPLE 81

BIS[2-AMINO-5-(HYDROXYBENZYL)PHENYL] DISELENIDE

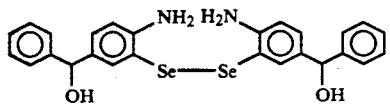

Using the procedure described in Example 65, but replacing 6-benzoylbenzoselenazolinone by 6-[phenyl(hydroxy)methyl]benzoselenazolinone, the product of the title is obtained.
Recrystallization solvent: toluene
Yield: 50%
Melting point: >270° C.
Percentage composition: Calculated: C 56.33, H 4.36, N 5.05, Found: C 56.47, H 4.34, N 4.97.
Infrared spectrometry: 1600 cm$^{-1}$ ν CHAr 3340 cm$^{-1}$ ν CH+OH
Nuclear Magnetic Resonance Spectrometry: $^1$H, (CD$_3$)$_2$SO δ: 5.50 ppm, doublet 2H C$\underline{H}$OH

EXAMPLE 82

BIS[2-(METHYLAMINO)PHENYL ] DISELENIDE

Using the procedure described in Example 65, but replacing 6-benzoylbenzoselenazolinone by 3-methylbenzoselenazolinone, the product of the title is obtained.
Melting point: 88° C.

PHARMACOLOGICAL STUDY OF THE PRODUCTS OF THE INVENTION

EXAMPLE 83

ACUTE TOXICITY

The acute toxicity was assessed after oral administration of increasing doses (0.1, 0.25, 0.50, 0.75 and 1 g.kg$^{-1}$) to batches of five mice (20±2 grams). The animals were observed at regular intervals during the first day, and daily during the two weeks following the treatment.

It is apparent that the compounds of the invention are completely non-toxic. No death was observed after administration of a dose of 1 g.kg$^{-1}$. No disorder is noted after administration of this dose.

EXAMPLE 84

MEASUREMENT OF GLUTATHIONE PEROXIDASE (GPx) ACTIVITY

Glutathione peroxidase is an enzyme which catalyzes the reduction of peroxides to alcohols. The selenium-containing products have a glutathione peroxidase type activity.

The reaction employs reduced glutathione (GSH) as a cofactor, and produces oxidized glutathione (GSSG) (Phase 1). An excess of glutathione reductase combined with NADPH in reduced form as a cofactor enables the concentration of reduced glutathione to be maintained at its initial level.

Thus, the oxidation of NADPH observed in UV at 340 nm is directly linked to the glutathione peroxidase activity. This method is reputedly reliable for comparing the activities of different products (A. WENDEL, Glutathione peroxidase. Methods in Enzymol. 1981, 77, 324–333 and B. FARAJI, H. K. KANGE and J. L. VALENTINE, Methods compared for determining glutathione peroxidase activity in blood. Clin. Chem. 33, 539–549, 1987).

Some of the products of the invention have shown a glutathione peroxidase activity approximately three times as intense as that of the compound which forms the subject of European Patent Application No. 0.044,971.

EXAMPLE 85

DEMONSTRATION OF A LIPID PEROXIDATION-INHIBITORY ACTIVITY

After decapitation, the cerebral hemispheres of male Wistar rats are homogenized. The homogenate is incubated by itself for 30 minutes at 37° C. to study spontaneous peroxidation, and in the presence of a free-radical generating system, iron/ascorbate, to study induced peroxidation. The intensity of lipid peroxidation in the presence and absence of the compounds of the invention is measured by determination of the substances reacting with thiobarbituric acid (SRTBA) expressed as mmol of malonaldehyde by a method derived from that of Yagi (Yagi K. Biochem. Med., 1976, 15,212–216). It is apparent that the products of the invention have an advantageous activity in this test.

EXAMPLE 86

STUDY OF PLATELET AGGREGATION-INHIBITORY ACTIVITY

A platelet-rich plasma is prepared from citrated human blood originating from donors who have taken no medication during the ten days preceding donation of the sample.

Platelet aggregation in this plasma medium is studied by turbidimetry, employing an agonist: arachidonic acid. The products of the invention are added to the plasma three minutes before the agonist.

The products of the invention manifest a significant antagonist activity with respect to platelet aggregation.

EXAMPLE 87

STIMULATION OF IMMUNE RESPONSES

Sheep red cells were administered to groups of six mice. These groups of mice were then treated subcutaneously with the compounds of the invention for six days, and a control group was treated with a placebo. The mice were then left undisturbed for four weeks and thereafter received a booster injection of sheep red cells without receiving further administrations of a product of the invention. The immune response was evaluated 3 days after the booster injection. It showed a statistical increase in the group treated with the compounds of the invention.

EXAMPLE 88

STUDY OF HYPOGLYCEMIC ACTIVITY

Male KK mice are placed in cages at the age of eight weeks. They are used for the experiment when their weight is greater than 40 grams at the age of 4–5 months.

The compound of the invention is suspended in acacia syrup. Each test compound is administered orally 18 hours before drawing a blood sample.

The blood is collected by drawing from the caudal vein into a hematocrit tube, and then centrifuged. The plasma is collected and an assay of the blood sugar level is performed.

It is apparent that the compounds of the invention significantly decrease the blood sugar level.

EXAMPLE 89

STUDY OF ANTI-INFLAMMATORY ACTIVITY

Measurement of cyclooxygenase inhibition:

Cyclooxygenase activity is measured using washed human platelets, in the presence and absence of the claimed compounds, after activation by thrombin (Cerletti et al, J. Clin. Invest., 1986, 78, 323–326).

The thromboxane $B_2$ produced is assayed by a radioimmunological method. It is apparent that, at a concentration of $10^{-5}M$, some products of the invention antagonize cyclooxygenase to the extent of 90 to 95%.

Measurement of lipoxygenase inhibition:

Lipoxygenase activity is measured using washed human polymorphonuclear cells, in the presence and absence of the claimed compounds, after activation by calcium (A23187). The leukotriene $B_4$ ($LTB_4$) produced is measured by radioimmunoassay (Gresele, P et al, Biochem. Biophys. Res. Comm., 1986, 137, 334–342). It is apparent that, at a concentration of $10^{-5}M$, some products of the invention antagonize lipoxygenase to the extent of 90 to 97%.

It is apparent that the products of the invention are endowed with mixed-type anti-inflammatory activity, being simultaneously lipoxygenase and cyclooxygenase inhibitors.

Inhibition of carrageenan-induced edema:

The anti-inflammatory potential of the compounds of the invention was also investigated on a model of acute inflammation caused by the subcutaneous injection of a carrageenan solution into the rat hind foot, according to a technique based on the method of WINTER, C. A., E. A. RISLEY and G. N. NUSS (Proc. Soc. Exp. Med. 111, 554, 1962). The rats (100–120 g), randomized in batches of 8, were treated with the products of the invention (the controls receive the excipient) 1 hour before the local injection of a 0.5% solution of carrageenan (Sigma type IV; 0.1 ml per rat). The edema is determined 3 hours after injection, by plethysomometric measurement (UGO BASILE water plethysmometer) of the volume of each of the hind feed (edema=-volume of the inflamed foot minus the volume of the non-inflamed foot).

It is apparent that the products of the invention at a dose of 3 mg.kg$^{-1}$ significantly decrease the volume of the edema.

EXAMPLE 90

STUDY OF ANTIOXIDANT PROPERTIES

The property of 2,2'-azobis(2-amidinopropane) hydrochloride (AAPH) (oxidizing agent), which consists in generating free radicals at a constant rate, is used for inducing the lyses of human red cells.

The inhibition of the hemolysis is calculated for the compounds under study by comparison with the percentage hemolysis obtained with the AAPH control, by assaying the hemoglobin liberated by measuring the optical density at 403 nm.

The products of the invention manifest an advantageous activity in this test.

EXAMPLE 91

STUDY OF ANALGESIC ACTIVITY

Activity agent pain was investigated in mice (23–25 g) according to a protocol based on the technique described by SIEGMUND (SIEGMUND E. A., R. A. CADMUS & GOLU, J. Pharm. Exp. Therm. 119, 1874, 1954). The mice, randomized in batches of 12 animals, received the treatment orally (excipient of the controls) 1 hour before the intraperitoneal injection of a 0.02% aqueous-alcoholic solution of phenyl-p-benzoquinone (Sigma). The writhing movements are counted between the 5th and 10th minute after injection.

The percentage activity obtained was evaluated for each dose (% decrease in the number of writhing movement in the treated animals relative to the controls). An $ED_{50}$, the dose producing a 50% activity, was determined for each product.

It was apparent that some compounds of the invention possess a very advantageous analgesic activity. Thus, some compounds of the invention have an $ED_{50}$ in the region of 10 mg.kg$^{-1}$.

EXAMPLE 92

ACTIVITY WITH RESPECT TO LIPID BALANCE

A study of the effect of the products of the invention or lipid balance is carried out after repeated oral administration of the compounds of the invention for 7 days.

The test is carried out on the groups of 12 Iffa Credo mice weighing 25±1 g on the day on which the treatment is started. One group receives a placebo. The other group of mice receives fenofibrate at a dose of 300 mg.kg$^{-1}$/day. The other groups of mice receive the products of the invention at a dose of 30 mg.kg$^{-1}$/day. An assay of triglycerides and total, free and esterified cholesterol reveals a significant decrease in these parameters, greater than that obtained with fenofibrate (at a 10-fold higher dose).

EXAMPLE 93

STUDY OF THE ANTIHYPOXIC ACTIVITY OF THE COMPOUNDS OF THE INVENTION

Male rats weighing between 300 and 350 g are anesthetized with pentobarbital sodium (60 mg.kg$^{-1}$ i.p.). The animals are heparinized and, after opening of the abdomen and sectioning of the diaphragm, the heart is removed. It is then attached by the aorta to the profusion cannula and perfused via the left atrium according to the protocol of Rochette et al (American Heart Journal, 107, 1132–1141).

After 15 minutes' perfusion, the substance under study is added to the perfusion fluid (Krebs); it is maintained in this fluid until the end of the experiment. A ligature is applied to the left coronary artery 15 minutes after the addition of the substance. It is maintained for 10 minutes, and the reperfusion occurring following removal of the ligature is studied over 10 minutes.

In the presence of the products of the invention, a significant improvement is noted in the following parameters:
coronary flow rate
aortic flow rate
cardiac flow rate
heart rate

EXAMPLE 94

PHARMACEUTICAL COMPOSITIONS

TABLETS

Tablets containing 10 mg of bis(2-methylamino-5-benzoylphenyl) diselenide

| Preparation formula for 1000 tablets: | |
|---|---|
| Bis(2-methylamino-5-benzoylphenyl) diselenide | 10 g |
| Wheat starch | 15 g |
| Corn starch | 15 g |
| Lactose | 65 g |
| Magnesium stearate | 2 g |
| Silica | 1 g |
| Hydroxypropyl cellulose | 2 g |

I claim:

1. A compound selected from those of formula (I):

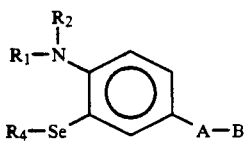

in which:

$R_4$ forms a —C=O groups with $R_1$, $R_2$ represents hydrogen or lower alkyl optionally substituted with one or more halogen atoms or with hydroxyl or, substituted with a group $NR_5R_6$, in which $R_5$ and $R_6$, which may be identical or different, each represent, independently of one another, hydrogen, lower alkyl, aryl, substituted aryl, aryl(lower alkyl), or substituted aryl(lower alkyl), or alternatively, $R_5$ and $R_6$, with the nitrogen atom which carries them, form a heterocyclic system, A represents CO, CHOH, or $CH_2$, B represents hydrogen, lower alkyl, cycloalkyl having 3 to 8 carbon atoms, inclusive, lower alkenyl, lower alkynyl, aryl or substituted aryl, heteroaryl or substituted heteroaryl, aryl(lower alkyl), heteroaryl(lower alkyl), or substituted heteroaryl(lower alkyl), styryl, or substituted styryl, or A and B together represent hydrogen, on condition that, when A and B together represent hydrogen: then $R_2$ cannot represent methyl or hydrogen, on the understanding that:

the term heterocyclic in the definitions of $R_2$ represents a mono- or bicyclic system, each ring being five- or six-membered and including in its carbon skeleton one or more identical or different hetero atoms selected from nitrogen, oxygen, and sulfur, and optionally substituted with lower alkyl, aryl, aryl substituted with arylalkyl, substituted arylalkyl; heteroaryl, substituted heteroaryl; one or more halogen atoms, or lower alkoxy, the terms substituted qualifying the aryl, aryl(lower alkyl), heteroaryl and styryl groups in the definitions of $R_2$ and B means that these are substituted on the aromatic portion with one or more identical or different groups selected from lower alkyl, lower alkoxy, hydroxyl, trifluoromethyl, amino, and carboxyl, or with one or more halogen atoms, lower alkyl, lower alkoxy, lower alkenyl, and lower alkynyl mean linear or branched groups having 1 to 6 carbon atoms, inclusive, aryl means a group selected from phenyl and naphthyl, heteroaryl means a mono- or bicyclic aromatic group, each ring being five- or six-membered, the two rings collectively including in their carbon skeleton one to three hetero atoms selected from nitrogen, oxygen, and sulfur, its isomers, epimers and diastereoisomers, and, when B comprises carboxyl or phenolic hydroxyl, its addition salts with a pharmaceutically-acceptable base, as well as, when $R_2$ represents amino, its addition salts with a pharmaceutically-acceptable acid.

2. A compound as claimed in claim 1, selected from those in which $R_1$ forms a CO group with $R_4$, of formula (I/D1):

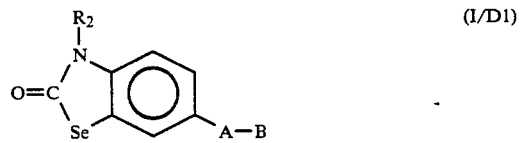

in which $R_2$, A and B have the same definitions as in the formula (I), as an addition salt thereof with a pharmaceutically-acceptable acid or base.

3. A compound as claimed in claim 1, in which A-B represents hydrogen, its isomers and, where appropriate, its addition salts with a pharmaceutically-acceptable acid or base.

4. A compound as claimed in claim 1, selected from those of formula (I/S):

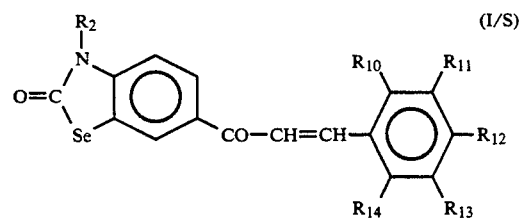

in which $R_2$ has the same definition as in claim 1 and $R_{10}$, $R_{11}$, $R_{12}$, $R_{13}$ and $R_{14}$, which may be identical or different, represent, independently of one another, hydrogen, lower alkyl, lower alkoxy, hydroxyl, trifluoromethyl, amino, or halogen, its isomers and, where appropriate, its addition salts with a pharmaceutically-acceptable acid or base.

5. A compound as claimed in claim 1, selected from those for which A represents CO and B represents phenyl, its isomers and, where appropriate, its addition salts with a pharmaceutically-acceptable acid.

6. A compound as claimed in claim 1, selected from 6-(3,5-di-tert-butyl-4-hydroxycinnamoyl)benzoselenazolinone, its isomers and its addition salts with a pharmaceutically-acceptable base.

7. A compound as claimed in claim 1, selected from 3-methyl-6-(3,5-di-tert-butyl-4-hydroxycinnamoyl) benzoselenazolinone, its isomers and its addition salts with a pharmaceutically-acceptable base.

8. A compound as claimed in claim 1, selected from 6-benzoylbenzoselenazolinone, and its addition salts with a pharmaceutically-acceptable base.

9. A compound as claimed in claim 1, which is selected from 6-8 phenyl(hydroxy)methyl] benzoselenazolinone and an addition salt thereof with a pharmaceutically-acceptable base.

10. A compound selected from those of formula (I):

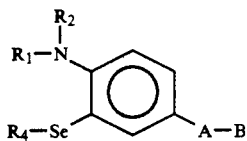

in which:
$R_1$ represents hydrogen or $CO-NR_7R_8$, wherein
$R_7$ and $R_8$, which may be identical or different, represent hydrogen, lower alkyl, or cycloalkyl having 3 to 8 carbon atoms inclusive, or aryl or substituted aryl or aryl(lower alkyl) or substituted aryl(lower alkyl), or, with the nitrogen atom which carries them, form a heterocyclic system,
$R_4$ represents:

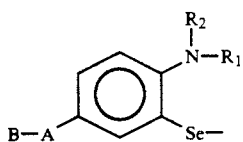

$R_2$ represents hydrogen or lower alkyl optionally substituted with one or more halogen atoms or with hydroxyl or substituted with a group $NR_5R_6$, in which $R_5$ and $R_6$, which may be identical or different, each represent, independently of one another, hydrogen, lower alkyl, aryl, substituted aryl, aryl(lower alkyl), or substituted aryl(lower alkyl), or alternatively $R_5$ and $R_6$, with the nitrogen atom which carries them, form a heterocyclic system,
A represents CO, CHOH, or $CH_2$,
B represents hydrogen, lower alkyl, cycloalkyl having 3 to 8 carbon atoms, inclusive, lower alkenyl, lower alkynyl, aryl or substituted aryl, heteroaryl or substituted heteroaryl, aryl(lower alkyl), heteroaryl(lower alkyl), or substituted heteroaryl(lower alkyl), styryl or substituted styryl, or A and B together represent hydrogen when $R_1$ represents $-CO-NR_7R_8$,
on the understanding that:
the term heterocyclic in the definitions of $R_1$ and $R_2$ represents a mono- or bicyclic system, each ring being five- or six-membered and including in its carbon skeleton one or more identical or different hetero atoms selected from nitrogen, oxygen, and sulfur, and optionally substituted with lower alkyl, aryl, aryl substituted with arylalkyl, substituted arylalkyl; heteroaryl, substituted heteroaryl; one or more halogen atoms, or lower alkoxy, the term substituted qualifying the aryl, aryl(lower alkyl), heteroaryl and styryl groups in the definitions of $R_1$, $R_2$ and B means that these are substituted on the aromatic portion with one or more identical or different groups selected from lower alkyl, lower alkoxy, hydroxyl, trifluoromethyl, amino, and carboxyl, or with one or more halogen atoms, lower alkyl, lower alkoxy, lower alkenyl, and lower alkynyl mean linear or branched groups having 1 to 6 carbon atoms, inclusive, aryl means a group selected from phenyl and naphthyl, heteroaryl means a mono- or bicyclic aromatic group, each ring being five- or six-membered, the two rings collectively including in their carbon skeleton one to three hetero atoms selected from nitrogen, oxygen, and sulfur, its isomers, epimers and diastereoisomers, and, when B comprises carboxyl and phenolic hydroxyl or, when $R_1$ represents hydrogen, its addition salts with a pharmaceutically-acceptable base, as well as, when $R_2$ represents amino, its addition salts with a pharmaceutically-acceptable acid.

11. A compound as claimed in claim 10, selected from those of formula (I/G1):

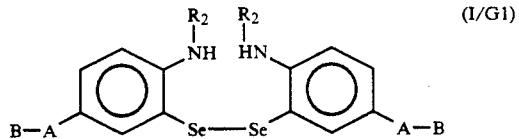

in which A, B and $R_2$ have the same definitions as in formula (I), and, where appropriate, its addition salts with a pharmaceutically-acceptable acid or base.

12. A compound as claimed in claim 1, selected from those of formula (I/F):

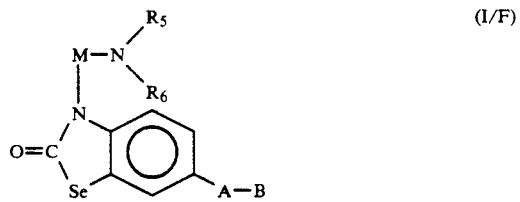

in which M represents lower alkyl and A, B, $R_5$ and $R_6$ have the same definitions in formula (I), its isomers and its addition salts with a pharmaceutically-acceptable acid or base.

13. A compound as claimed in claim 10, selected from bis(2-amino-5-benzoylphenyl) diselenide, and its addition salts with a pharmaceutically-acceptable acid.

14. A compound as claimed in claim 10, which is selected from bis(2-methylamino-5-benzoylphenyl) diselenide, and its addition salts with a pharmaceutically-acceptable acid.

15. A compound as claimed in claim 10, which is bis[2-(3,3-dimethylureido)phenyl] diselenide.

16. A compound as claimed in claim 10, which is selected from {2-amino-5-[phenyl(hydroxy)methyl]-phenyl} diselenide, and its addition salts with a pharmaceutically-acceptable base.

17. A compound as claimed in claim 10, which is bis[2-(3,3-dimethylureido)-5-benzoylphenyl] diselenide.

18. A compound as claimed in claim 10, which is selected from bis(2-amino-5-acetylphenyl) diselenide, and its addition salts with a pharmaceutically-acceptable acid.

19. A pharmaceutical composition useful in alleviating inflammatory disorders containing as active principle at least one compound selected from those of formula (I):

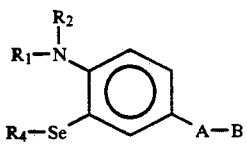

in which:

$R_1$ represents hydrogen or $CO-NR_7R_8$, wherein $R_7$ and $R_8$, which may be identical or different, represent hydrogen, lower alkyl, or cycloalkyl having 3 to 8 carbon atoms inclusive, or aryl or substituted aryl or aryl(lower alkyl) or substituted aryl(lower alkyl), or, with the nitrogen atom which carries them, form a heterocyclic system, $R_4$ represents:

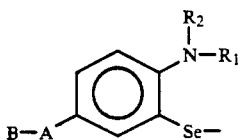

or alternatively:

$R_4$ forms a $-C=O$ group with $R_1$, $R_2$ represents hydrogen or lower alkyl optionally substituted with one or more halogen atoms or with hydroxyl or, when $R_1$ forms a CO group with $R_4$, substituted with a group $NR_5R_6$, in which $R_5$ and $R_6$, which may be identical or different, each represent, independently of one another, hydrogen, lower alkyl, aryl, substituted aryl, aryl(lower alkyl), or substituted aryl(lower alkyl), or alternatively $R_5$ and $R_6$, with the nitrogen atom which carries them, form a heterocyclic system, A represents CO, CHOH, or $CH_2$, B represents hydrogen, lower alkyl, cycloalkyl having 3 to 8 carbon atoms, inclusive, lower alkenyl, lower alkynyl, aryl or substituted aryl, heteroaryl or substituted heteroaryl, aryl(lower alkyl), heteroaryl(lower alkyl), or substituted heteroaryl(lower alkyl), styryl, or substituted styryl, or A and B together represent hydrogen, on condition that, when A and B together represent hydrogen:
if $R_1$ forms a CO group with $R_4$, then $R_2$ connot represent methyl or hydrogen,
if $R_1$ does not form a CO group with $R_4$, then $R_1$ and $R_2$ cannot simultaneously represent a hydrogen atom, on the understanding that:
the term heterocyclic in the definitions of $R_1$ and $R_2$ represents a mono- or bicyclic system, each ring being five- or six-membered and including in its carbon skeleton one or more identical or different hetero atoms selected from nitrogen, oxygen, and sulfur, and optionally substituted with lower alkyl, aryl, aryl substituted with arylalkyl, substituted arylalkyl; heteroaryl, substituted heteroaryl; one or more halogen atoms, or lower alkoxy, the term substituted qualifying the aryl, aryl(lower alkyl), heteroaryl and styryl groups in the definitions of $R_1$, $R_2$ and B means that these are subsituted on the aromatic portion with one or more identical or different groups selected from lower alkyl, lower alkoxy, hydroxyl, trifluoromethyl, amino, and carboxyl, or with one or more halogen atoms, lower alkyl, lower alkoxy, lower alkenyl, and lower alkynyl mean linear or branched groups having 1 to 6 carbon atoms, inclusive, aryl means a group selected from phenyl and naphthyl, heteroaryl means a mono- or bicyclic aromatic group, each ring being five- or six-membered, the two rings collectively including in their carbon skeleton one to three hetero atoms selected from nitrogen, oxygen, and sulfur, its isomers, epimers and diastereoisomers, and, when B comprises carboxyl or phenolic hydroxyl or when $R_1$ represents hydrogen, its addition salts with a pharmaceutically-acceptable base, as well as, when $R_2$ represents amino, its addition salts with a pharmaceutically-acceptable acid, in combination with one or more pharmaceutically-acceptable excipients or vehicles.

20. A method of treating a living animal afflicted with an inflammatory disorder comprising the step of administering to the said living animal an amount of a compound selected from those of formula (I):

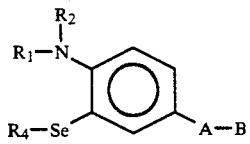

in which:

$R_1$ represents hydrogen or $CO-NR_7R_8$, wherein $R_7$ and $R_8$, which may be identical or different, represent hydrogen, lower alkyl, or cycloalkyl having 3 to 8 carbon atoms inclusive, or aryl or substituted aryl or aryl(lower alkyl) or substituted aryl(lower alkyl), or, with the nitrogen atom which carries them, form a heterocyclic system, $R_4$ represents:

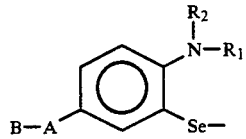

or alternatively:

$R_4$ forms a $-C=O$ group with $R_1$, $R_2$ represents hydrogen or lower alkyl optionally substituted with one or more halogen atoms or with hydroxyl or, when $R_1$ forms a CO group with $R_4$, substituted with a group $NR_5R_6$, in which $R_5$ and $R_6$, which may be identical or different, each represent, independently of one another, hydrogen, lower alkyl, aryl, subsituted aryl, aryl(lower alkyl), or substituted aryl(lower alkyl), or alternatively $R_5$ and $R_6$, with the nitrogen atom which carries them, form a heterocyclic system, A represents CO, CHOH, or $CH_2$, B represents hydrogen, lower alkyl, cycloalkyl having 3, to 8 carbon atoms, inclusive, lower alkenyl, lower alkynyl, aryl or substituted aryl, heteroaryl or substituted heteroaryl, aryl(lower alkyl), heteroaryl(lower alkyl), or substituted heteroaryl(lower alkyl), styryl, or substituted styryl, or A and B together represent hydrogen, on condition that, when A and B together represent hydrogen:

if $R_1$ forms a CO group with $R_4$, then $R_2$ cannot represent methyl or hydrogen, if $R_1$ does not form a CO group with $R_4$, then $R_1$ and $R_2$ cannot simultaneously represent a hydrogen atom, on the understanding that:

the term heterocyclic in the definitions of $R_1$ and $R_2$ represents a mono- or bicyclic system, each ring being five- or six-membered and including in its carbon skeleton one or more identical or different hetero atoms selected from nitrogen, oxygen, and sulfur, and optionally substituted with lower alkyl, aryl, aryl substituted with arylalkyl, substituted arylalkyl; heteroaryl, substituted heteroaryl; one or more halogen atoms, or lower alkoxy, the term substituted qualifying the aryl, aryl(lower alkyl), heteroaryl and styryl groups in the definitions of $R_1$, $R_2$ and B means that these are substituted on the aromatic portion with one or more identical or different groups selected from lower alkyl, lower alkoxy, hydroxyl, trifluoromethyl, amino, and carboxyl, or with one or more halogen atoms, lower alkyl, lower alkoxy, lower alkenyl, and lower alkynyl mean linear or branched groups having 1 to 6 carbon atoms, inclusive, aryl means a group selected from phenyl and naphthyl, heteroaryl means a mono- or bicyclic aromatic group, each ring being five- or six-membered, the two rings collectively including in their carbon skeleton one to three hetero atoms selected from nitrogen, oxygen, and sulfur, its isomers, epimers and diastereoisomers, and, when B comprises carboxyl or phenolic hydroxyl or when $R_1$ represents hydrogen, its addition salts with a pharmaceutically-acceptable base, as well as, when $R_2$ represents amino, its addition salts with a pharmaceutically-acceptable acid, which is effective for alleviation of said disorder.

* * * * *

UNITED STATES PATENT AND TRADEMARK OFFICE
CERTIFICATE OF CORRECTION

PATENT NO. : 5,246,951

DATED : September 21, 1993

INVENTOR(S) : Vincent Galet, Marie-Pierre Vaccher, Daniel Lesieur, Pierre Renard, Daniel H. Caignard, Jean-Francois Renaud de la Faverie, Gérard Adam.

It is certified that error appears in the above-indentified patent and that said Letters Patent is hereby corrected as shown below:

Col. 1, line 10; correct the spelling of "benzoselenazol".
Col. 1, line 14; change the period to a comma in the patent number.
Col. 3, line 26; the R group should read -- $R_2'$ --.
Col. 5, line 1; the R group should read -- $R_1$ --.
Col. 7, line 6; insert -- of -- after "amine".
Col. 9, line 7; delete "1" after "50".
Col. 9, line 17; change "80°" to -- 58° --.
Col. 10, line 2; insert a space after "6".
Col. 10, line 22; replace "inhibited" with -- obtained --.
Col. 10, line 37; Capitalize the "H" in "heating".
Col. 10, line 67; correct the spelling of "hydroxybenzaldehyde".
Col. 12, last two lines; change "$cm^{-1}$ m" to -- $cm^{-1}$ $\nu$ -- in three (3) places.
Col. 13, line 1; correct the spelling of "Oxobenzoselenazolin".
Col. 13, line 10; change "$cm^{-1}$ m" to -- $cm^{-1}$ $\nu$ --.
Col. 13, lines 17 and 18; change "$cm^{-1}$ m" to -- $cm^{-1}$ $\nu$ --, in two (2) places.
Col. 13, line 54; change "$cm^{-1}:\lambda$" to -- $cm^{-1}$ $\nu$ --.
Col. 14, line 4; change "CH-" to -- $CH_2$- --.
Col. 14, line 5; delete "$_2$-" at the beginning of the line.
Col. 14, line 14; change "ml" to -- mol --.
Col. 14, line 36; change "$CH_3$" to -- $CH_2$ --.
Col. 14, line 45; insert a space between "a" and "round".
Col. 14, line 56; delete the final "e" in the line, leaving the hyphen.
Col. 14, line 57; correct the spelling of "ethyl".
Col. 14, line 59; insert a hyphen after "3".
Col. 15; line 21; insert a hyphen after "3".
Col. 15, line 47; insert a hyphen after "4".
Col. 15, line 48; delete the final "e", leaving the hyphen.

UNITED STATES PATENT AND TRADEMARK OFFICE
CERTIFICATE OF CORRECTION

PATENT NO. : 5,246,951　　　　　　　　　Page 2 of 3

DATED　　　 : September 21, 1993

INVENTOR(S) : Vincent Galet, Marie-Pierre Vaccher, Daniel Lesieur, Pierre Renard, Daniel H. Caignard, Jean-Francois Renaud de la Faverie, Gérard Adam.

It is certified that error appears in the above-indentified patent and that said Letters Patent is hereby corrected as shown below:

Col. 15, line 49;　correct the spelling of "ethane".
Col. 16, line 24;　correct the spelling of "benzoselenazolinone".
Col. 16, line 28;　insert a comma after "C.".
Col. 16, line 36;　change "DMSO-$d_5$" to -- DMSO-$d_6$ --.
Col. 17, line 21;　insert a hyphen before "phenylpiperazine".
Col. 17, line 32;　insert a hyphen after "[4".
Col. 17, line 40;　insert a hyphen after "3-(1".
Col. 18, line 4;　capitalize the "u" in "using".
Col. 18, line 10;　change "Benzylaminomethyl" to -- Benzylaminoethyl --.
Col. 18, line 22;　change "3-[2-(2-" to -- 3-[2-(4- --.
Col. 20, line 7;　insert a hyphen after "6".
Col. 20, line 11;　delete the final "E", leaving the hyphen.
Col. 20, line 12;　correct the spelling of "ETHYL".
Col. 22, line 36;　insert a hyphen after "3".
Col. 22, line 36;　insert closed parenthesis at the end of the word "TRIFLUOROMETHYLBENZYL", and before the hyphen.
Col. 23, line 46;　insert a hyphen after "6".
Col. 23, line 55;　change "an" to -- and --.
Col. 23, line 58;　change "⅓" to -- ⅔ --.
Col. 23, line 59;　change "⅔" to -- ⅓ --.
Col. 23, line 63;　change "3.86" to -- 3.89 --.
Col. 24, line 16;　change "¾" to -- ⅓ --.
Col. 26, line 16;　insert a straight line completely under the line.
Col. 26, line 26;　change the period in the patent number to a comma.
Col. 29, line 60;　after the colon, insert -- if $R_1$ forms a CO group with $R_4$, --.

UNITED STATES PATENT AND TRADEMARK OFFICE
CERTIFICATE OF CORRECTION

PATENT NO. : 5,246,951
DATED : September 21, 1993
INVENTOR(S) : Vincent Galet, et al It is certified that error appears in the above-indentified patent and that said Letters Patent is hereby corrected as shown below:

Col. 31, line 13;   change "8" to --[--.

Signed and Sealed this

Sixteenth Day of August, 1994

Attest:

BRUCE LEHMAN

*Attesting Officer*  *Commissioner of Patents and Trademarks*